United States Patent [19]

Franzmann

[11] 4,380,646

[45] Apr. 19, 1983

[54] METHOD FOR THE N-ACYLATION OF AMINOCARBOXYLIC ACIDS

[75] Inventor: Giselher Franzmann, Witten, Fed. Rep. of Germany

[73] Assignee: Dynamit Nobel Aktiengesellschaft, Troisdorf, Fed. Rep. of Germany

[21] Appl. No.: 229,433

[22] Filed: Jan. 29, 1981

[30] Foreign Application Priority Data

Feb. 2, 1980 [DE] Fed. Rep. of Germany ....... 3003898

[51] Int. Cl.³ .................. C07D 209/20; C07C 103/34; C07C 103/76
[52] U.S. Cl. .................................... 548/502; 562/445; 562/446; 562/553; 562/559; 562/561; 562/575; 562/576; 548/344
[58] Field of Search ............... 260/326.14 T; 562/574, 562/445, 446, 559; 548/344, 502

[56] References Cited

U.S. PATENT DOCUMENTS 3,769,271 10/1973 Southard .................... 260/326.14 T Primary Examiner—Mary C. Lee
Assistant Examiner—D. B. Springer
Attorney, Agent, or Firm—Sprung, Horn, Kramer & Woods

[57] ABSTRACT

A process is disclosed for the prparation of an acylated aminocarboxylic acid which comprises contacting an aminocarboxylic acid, its alkali metal or alkaline earth metal salt with a low alkyl carboxylic acid ester of the formula $$R_1\text{-CO-O-}R_2,$$

wherein $R_1$ represents hydrogen or a straight-chain or branched or cyclic hydrocarbon moiety of 1 to 30 carbon atoms, which can be substituted if desired, and wherein $R_2$ represents a straight-chain, branched or cyclic hydrocarbon moiety of 1 to 8 carbon atoms in the presence of an alkali metal or alkaline earth metal alcoholate.

18 Claims, No Drawings

METHOD FOR THE N-ACYLATION OF AMINOCARBOXYLIC ACIDS

BACKGROUND OF THE INVENTION

1. Field of the Invention

The invention relates to a simple and inexpensive acylation process, especially for the acetylation of aminocarboxylic acids. Particularly expensive amino acids such as phenylalanine and tryptophan can thus be advantageously acylated.

It is known to acylate aminocarboxylic acids with the aid of carboxylic acid anhydrides or halides. The known methods result neither in high yields nor in products of high purity. Particularly, the acetylation of phenylalanine with acetic anhydride yields an impure product. The more one strives for an N-acetyl-phenylalanine of satisfactory purity, the greater is the excess of acetic anhydride that must be used. The acetic acid that is produced in acetylation with acetic anhydride interferes with the isolation of the product and prevents high yields of pure product.

Good yields and purities result from the acetylation of aminocarboxylic acids with ketene in accordance with German Offenlegungsschrift No. 2,741,081. However, ketene always has to be produced freshly in a generator and must be used immediately. This method, therefore, is profitable only with regard to relatively large quantities.

THE INVENTION

The problem has therefore existed of finding a method for the acylation of aminocarboxylic acids which gives products of high purity in a high yield at resonable cost. It has been found surprisingly that aminocarboxylic acids and their alkali or alkaline metal salts can be acylated substantially quantitatively with low-alkyl carboxylic acid esters in the presence of alkali metal alcoholates.

The subject matter of the invention is therefore a method of acylating aminocarboxylic acids which is characterized by the fact that aminocarboxylic acids whose alkali salts or alkaline earth salts are reacted in the presence of alkali metal alcoholates or alkaline earth metal alcoholates with low alkyl carboxylic acid esters of the general formula $R_1$-CO-O-$R_2$, wherein $R_1$ represents hydrogen or a straight-chain, branched or cyclic hydrocarbon moiety of 1 to 30 carbon atoms, which can be substituted if desired, and wherein $R_2$ represents a straight-chain, branched or cyclic hydrocarbon moiety of 1 to 8 carbon atoms, which can be substituted if desired.

Products of a high purity of 98 to 100% can be obtained in a high yield of at least 90% and generally 95 to 99%.

The method also permits an economical production of the acylamino acids even with the relatively small amounts involved in the case, for example, of phenylalanine and tryptophan.

The method of the invention can be practiced very simply: for example, the aminocarboxylic acid to be acylated, the alkali metal or alkaline earth metal alcoholate and the low-alkyl carboxylic acid ester are mixed and heated with stirring at temperatures of 40° to 200° C. After 2 to 4 hours the reaction has ended. Excess low-alkyl carboxylic acid ester and alcohol released from the alkali alcoholate and from the ester during the reaction can be distilled out. The residue is processed by conventional methods. For example, water is added and the N-acetylamino acid is precipitated with an acid, of the alkali metal salts of the N-acylamino acids are obtained.

The composition of the reaction mixture can vary widely. If a monobasic aminocarboxylic acid and an alkali metal alcoholate are used, one mole of alkali alcoholate is required per mole of amino acid for the formation of the alkali metal salt. However, the corresponding alkali salts of the aminocarboxylic acids can also be used. An excess of alkali metal alcoholate above the equimolecular amount is required as a catalyst for the acylation. Since the products put in often contain traces of water, the excess of alkali metal alcoholate will be fairly generous. For example, it is preferable to use a total of 1.2 to 2.0 moles, and very preferable 1.4 to 1.6 moles of alkali metal alcoholate, per mole of aminocarboxylic acid for the mositure-free formation of salt and as catalyst. Below about 1.2 moles of alcoholate per mole of amino acid, the yields are poorer unless traces of water are not carefully excluded. The use of more than two molar equivalents of alcoholate per mole of aminocarboxylic acid is, as a rule, unnecessary. In the case of the use of alkali salts, the amount of the alcoholate is reduced by the amount of alkali already present, and, in the case of polybasic aminocarboxylic acids, it is increased by the amount required for the additional salt formation. When alkaline earth metal alcoholates are used, equivalent stoichiometric amounts thereof are employed.

The low-alkyl carboxylic acid ester is to be used at least in a 1:1 molar ratio with respect to the amino groups to be acylated. Usually an excess of 50 to 500 mol-% is used, especially in order to obtain a stirrable mixture, ideally a clear solution, in the reaction. In many cases it is advantageous to add a solvent or a solubilizer to the three components, namely the aminocarboxylic acid, alcoholate and carboxylic acid ester. For example, an alcohol is used, and then the required amount of the carboxylic acid ester can be diminished. Obviously, in this case, the same alcohol can be used as that which is released in the reaction from the alkali alcoholate and from the lower alkyl carboxylic acid ester, although other alcohols which function as a solvent can be employed. Thus, the alkyl moieties of the alcoholate, the ester and any alcohol that is added may, however, be of any kind, i.e., they can be the same or different.

The reaction temperature is preferably at 50° to 100° C., and very preferably at the boiling point of the reaction mixture, although above about 40° C. it can vary widely. Temperatures less than about 40° C. are less desirable since they reduce the speed of the reaction. Higher temperatures facilitate the stirring of the mixture and the formation of clear solutions.

If the acylation of optically active amino acids is desired without racemation, it is recommendable to keep the reaction temperature as low as possible, but at the same time to make the time of reaction as short as possible.

Elevated pressure up to 50 bar can be used, but it has little to no effect on the outcome of the reaction. The process is, therefore, preferably performed at atmospheric pressure.

The term "aminocarboxylic acids", as used herein, refers to any monobasic or polybasic carboxylic acids containing one or more primary or secondary, preferably aliphatic amino groups. Of these, for reasons of necessity, the alpha amino-carboxylic acids of the structure of the natural amino acids are preferred. The aminocarboxylic acids can be of synthetic or natural origin. Examples of such amino acids are alanine, valine, methionine, serine, phenylalanine, tyrosine, tryptophan, 3,4-dihydroxyphenylalanine (DOPA), arginine, aspartic acids, glutamic acid, lysine, asparagine, glutamine, glycine, choline, threonine, histidine, cystein, isoleucine, and leucine.

With respect to the low carboxylic acid esters employed, it is preferred that the moieties $R_1$ and $R_2$ in the case when they represent a hydrocarbon moiety represent an alkyl, alkenyl or alkanyl moiety or a cyclic counterpart thereof. It is particularly contemplated that $R_2$ represent a straight chain or branched alkyl radical or a cyclo alkyl radical. $R_2$ can also represent an aralkyl radical such as the benzyl radical. With respect to the alcoholates of the alkali metal or alkaline earth metals, these alcoholates can be aromatic or aliphatic alcohols. It is particularly contemplated that they are aliphatic alcohols, especially alkanols although it should be understood that other alcohols such as alcohols of saturated and unsaturated hydrocarbons, e.g. alcohols of alkenes and alkines can also be used. The alcohol moiety of the alcoholate preferably has between 1 and 6 carbon atoms, especially 1 and 3 carbon atoms in its chain or ring. Preferably the alcoholates are alcoholates of $C_1$ to $C_4$ alkanols.

Preferred lower-alkyl carboxylic acid esters are those of the saturated, straight-chain monocarboxylic acids having 1 to 18, especially 1 to 4, carbon atoms, and very especially those of acetic acid and, of the alkyl groups of the esters, the ethyl and methyl group are preferred.

Examples of such low-alkyl carboxylic acid esters are: formic acid ethyl ester, acetic acid methyl ester, acetic acid ethyl ester, acetic acid isopropyl ester, acetic acid cyclohexyl ester, acetic acid benzyl ester, propionic acid methyl ester, butyric acid methyl ester, isobutyric acid ethyl ester, benzoic acid methyl ester, p-toluylic acid methyl ester, lauric acid methyl ester, myristic acid methyl ester, stearic acid methyl ester, and chloroacetic acid ethyl ester.

Alkali metal alcoholates which can be used in the process of the invention as catalyst and for the formation of salts include those of the general formula $R_2$-O-Me, wherein $R_2$ has the same meaning as above and Me is one mole of alkali metal or, if desired, half a mole of alkaline earth metal. Examples are: sodium methylate, sodium ethylate, potassium isopropylate.

Fundamentally, the use of alkaline earth alcoholates in the process of the invention is possible, but, on account of the poorer solubility of the amino acid or acylamino acid alkaline earth salts, it is not advantageous in most cases.

The free N-acylaminocarboxylic acid can be obtained as product, or its alkali or alkaline earth metal salts, depending on the case, or in the form of a salt solution.

The free N-acylamino acids can be precipitated with mineral acids such as hydrochloric acid or sulfuric acid in an at least equivalent amount.

The salts are obtained by adding water and producing them from the aqueous solution.

The excess of the low-alkyl carboxylic acid ester can be distilled out, in a mixture with alcohol if necessary, and re-used. If desired, water is added prior to such distillation so as to avoid difficulty in the distillation due to precipitating salts.

It is possible to produce acylamino acid alkali salts in pure form. For example, acetyl-DL-tryptophan sodium salt tetrahydrate crystallizes out of the reaction mixture if, after the addition of water and the removal of the alcoholester mixture from an acetylation mixture by distillation, the aqueous alkaline solution is neutralized with acid, e.g. acetic acid.

Acylamino acid alkali salts which are easily soluble in water, such as those of alanine, for example, can be obtained by concentrating the reaction mixture by evaporation without the addition of water. Then, either the desired product is separated from a solution partially concentrated by evaporation, which must be such that the alkali alcoholate still barely remains in solution, or the solution is concentrated by evaporation to the dry state, and thus a mixture of alkali alcoholate and acylamino acid alkali salt is obtained. By the admixture of an amount of acylamino acid equivalent to the excess alcoholate before or after distilling out the alcohol and the ester if any, anhydrous acylamino acid alkaline salt can be obtained.

If it is intended to use the acylamino acids and alkali salts for selective enzymatic saponification or deacylation, water can be added, the alcohol and the ester, if any, can be distilled out, and the solution can be neutralized with the corresponding acylamino acid to the pH range for enzymatic cleavage, and, after dilution, can be used directly to great advantage.

It is a special advantage of the present method that the products are formed and can be extracted in a very high yield of 95 to 99% and in very high purity.

The process is a very gentle one, so that it is suitable also and very especially for the acylation of expensive amino acids.

The acylation of the amino group is performed selectively by the method of the invention. The indolyl NH groups of tryptophan, for example, or the phenolic OH group of tyrosine, is not acylated.

The acylated amino acids are useful as:

1. raw materials for the production of optical active L-amino acids by enzymatic deacylation, by which in racemates of N-acyl amino acids selectively only the L-form is deacylated while the D-form is unchanged. The process is more closely described by I. Chibata, T. Tosa, T. Salo, T. Mori in Methods of Enzymatology VOL XLIV, p. 746 ff. Academic Press New York, 1976. Specific processes using immobilized AMANO-Acylase as enzyme are disclosed in our U.S.-patent applications Ser. No. 935,834 (corresponding to German Offenlegungsschrift 27 41 081) and Ser. No. 957,519 (corresponding to German Offenlegungsschrift 27 49 317 and 28 21 889).

2. The L-amino acids produced by the process noted above as well as acylated amino acids produced by the process of the present application are valuable food-additives.

EXAMPLES

Example 1

49.5 g of DL-phenylalanine (0.3 mol), 300 ml of acetic acid methyl ester and 24.3 g of sodium ethylate (0.45 mol) are mixed and refluxed with stirring for four hours. Excess acetic acid methyl ester is distilled out and the residue is dissolved with 200 ml of water. With 75 ml of 6 M hydrochloric acid, N-acetyl-DL-phenylalanine is precipitated, suction filtered after cooling to 5°–10° C., washed with 200 ml of water, and dried.

Yield: 59.0 g (95%); Acid number: 271 (calc. 271); Ash: 0.1%; Melting point: 152° C.

Example 2

495 g of DL-phenylalanine (3 mol), 245 g of sodium methylate (4.5 mol), 600 ml of acetic acid methyl ester, and 150 ml of methanol are mixed and refluxed for four hours with stirring. After the addition of 500 ml of water, the excess acetic acid methyl ester is distilled out in a mixture with methanol and water (580 ml). The solution is diluted with 1700 ml of water. The N-acetyl-DL-phenylalanine is precipitated with 138 ml of concentrated sulfuric acid, suction filtered after cooling to 10° C., then washed first with 2 liters and then again with 1.3 liters of water, and dried.

Yield: 582 g (94%); Acid number: 272 (calc. 271); Ash: less than 0.1%; Melting point: 154° C.

Example 3

The amino acid DL-leucine is acylated instead of DL-phenylalanine by the procedure of Example 1, with similar results.

Example 4

Example 2 is repeated. The water that is added after the reaction is the second wash water from a previous batch.

Yield: 608 g (98%); Acid number: 271 Ash: 0.05%; Melting point: 154°–155° C.

Example 5

49.5 g of L-phenylalanine, 24.3 g of sodium methylate, 60 ml of acetic acid methyl ester and 15 ml of methanol are mixed and refluxed for two hours with stirring. After the addition of 50 ml of water, excess acetic acid methyl ester is distilled off in a mixture with methanol and water (70 ml). The residue is diluted with 50 ml of water. With 40 ml of concentrated hydrochloric acid (12 M), N-acetyl-L-phenylalanine is precipitated, suction filtered after cooling to 5° to 10° C., washed with 300 ml of water, and dried.

Yield: 57.5 g (93%); Acid number: 274; Ash: less than 0.1%; Chloride: 0.17%.

Specific rotation (5% in ethanol):

$\alpha_D^{25} = +47.4°$ (=approximately 93% optical purity).

Example 6

49.5 g of DL-phenylalanine, 24.3 g of sodium methylate, 80 ml of acetic acid ethyl ester and 20 ml of methanol are mixed and refluxed for four hours with stirring. After the addition of 50 ml of water, excess acetic acid ethyl ester mixed with methanol, ethanol and water is distilled out (100 ml). The residue is diluted with 250 ml of water. With 39 ml of concentrated hydrochloric acid, N-acetyl-DL-phenylalanine is precipitated, suction filtered after cooling to 5°–10° C., washed with 200 ml of water, and dried.

Yield: 59.7 g (96%); Acid number: 270; Ash: less than 0.1%; Melting point: 154° C.; Chloride: 0.04%.

Example 7

Example 6 is repeated, but propionic acid methyl ester is used instead of acetic acid ethyl ester. Product: N-propionyl-DL-phenylalanine.

Yield: 63.5 g (96%); Acid number: 252 (calc. 254); Ash: less than 0.1%; Melting point: 133° C.; Chloride: 0.09%.

Example 8

61.3 g of DL-tryptophan (0.3 mol), 24.3 g of sodium methylate (0.45 mol), 80 ml of acetic acid methyl ester and 20 ml of methanol are mixed and refluxed for four hours with stirring. After the addition of 50 ml of water, 60 ml of a mixture of ester, alcohol and water is distilled off. The residue is diluted with 50 ml of water. With 38 ml of concentrated hydrochloric acid, Nα-acetyl-DL-tryptophan is precipitated, suction filtered after cooling to 10° C., washed with 300 ml of water and dried.

Yield: 70.2 g (95%); Acid number: 230 (calc. 228); Ash: less than 0.1%; Melting point: 203° C.; Chloride: 0.3%.

Example 9

Example 8 is repeated, but instead of precipitating with hydrochloric acid, first the residue is neutralized to pH 7 with 2 ml of concentrated hydrochloric acid. After cooling to 10° C., Nα-acetyl-DL-tryptophan sodium salt tetrahydrate is removed with a suction filter, washed with 20 ml of water and gently dried. 55.8 g of Nα-acetyl-DL-tryptophan sodium salt tetrahydrate is obtained, corresponding to 40.4 g of Nα-acetyl-DL-tryptophan.

Nα-acetyl-DL-tryptophan is precipitated from the mother liquor and washing filtrate with 15.7 ml of concentrated hydrochloric acid, and 29.7 g is obtained.

The total yield is 95%.

Example 10

44.7 g of DL-methionine (0.3 mol), 24.3 g of sodium methylate, 60 ml of acetic acid methyl ester and 15 ml of methanol are mixed and refluxed for four hours with stirring. After the addition of 50 ml of water, excess acetic acid methyl ester mixed with methanol and water is removed by distillation (60 ml). With 78 ml of semi-concentrated hydrochloric acid (6 mol), N-acetyl-DL-methionine is precipitated from the residue, suction filtered after cooling to 5° C., washed with 100 ml of water (10° C.) and dried. Additional product is obtained from the mother liquor by extraction with acetic acid ethyl ester and combined with the precipitated product.

Yield: 51.6 g (90%); Acid number: 293 (calc. 294); Ash: 0%; Melting point: 115° C.; Chloride: 0.09%.

Example 11

Example 6 is repeated, but instead of 80 ml of acetic acid ethyl ester, 100 g of lauric acid methyl ester is used. N-lauryl-DL-phenylalanine is formed in a good yield.

What is claimed is:

1. A process for the preparation of an

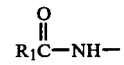

acylated 3,4-di-hydroxyphenyl alanine or a naturally occurring aminocarboxylic acid, which comprises the step of contacting its alkali metal or alkaline earth metal salt with a lower alkyl carboxylic acid ester of the formula

wherein $R_1$ represents hydrogen or a straight-chain or branched or cyclic hydrocarbon moiety of 1 to 30 carbon atoms, and wherein $R_2$ represents a straight-chain, branched or cyclic hydrocarbon moiety of 1 to 8 carbon atoms, in the presence of an alkali metal or alkaline earth metal alcoholate.

2. A process according to claim 1, wherein the process is carried out at a temperature of 40° to 200° C.

3. A process according to claim 2, wherein the process is carried out at a temperature of 50° to 100° C.

4. A process according to claim 1, wherein the process is carried out in the presence of an alkali metal alcoholate and there are employed 1.2 to 2.0 mols of alkali metal alcoholate per mol of amino carboxylic acid.

5. A process according to claim 1, wherein the low alkyl carboxylic acid ester is employed in an amount of 1 to 5 mols per mol of aminocarboxylic acid.

6. A process according to claim 1, wherein the process is carried out in the presence of an alkali metal alcoholate of a $C_1$–$C_4$ alkanol.

7. A process according to claim 6, wherein said alcoholate is sodium alcoholate.

8. A process according to claim 7, wherein said sodium alcoholate is sodium methylate.

9. A process according to claim 1, wherein said low alkyl carboxylic acid ester is a lower alkyl acetic acid ester.

10. A process according to claim 9, wherein said acetic acid ester is acetic acid methyl ester.

11. A process according to claim 1, wherein the process is carried out in the presence of a solvent or solubilizer.

12. A process according to claim 1, wherein said amino carboxylic acid is a synthetic or natural alpha amino carboxylic acid.

13. A process according to claim 12, wherein said amino carboxylic acid is selected from the group consisting of phenylalanine, tryptophan and methionine.

14. A process according to claim 1, wherein after the reaction the N-acylamino acid is obtained as an alkali salt or free amino acid.

15. A process according to claim 1, wherein the process is carried out in the presence of an alcohol.

16. A process according to claim 15, wherein said alcohol is the corresponding alcohol of the alkali or alkaline earth metal alcoholate employed.

17. A process according to claim 15, wherein said alcohol is the corresponding alcohol of $R_2$ and $R_2$ is a lower alkyl group.

18. A process according to claim 1, wherein the process is carried out in the absence of water.

* * * * *